United States Patent [19]

Buschhaus et al.

[11] 4,439,591

[45] Mar. 27, 1984

[54] PROCESS FOR THE PRODUCTION OF BLOCKED COMPOUNDS OPTIONALLY CONTAINING FREE HYDROXYL GROUPS AND THEIR USE FOR THE PRODUCTION OF POLYURETHANES

[75] Inventors: Hans-Ulrich Buschhaus, Cologne; Kurt Findeisen, Odenthal; Hans-Joachim Traenckner; Wolfgang Beer, both of Krefeld, all of Fed. Rep. of Germany

[73] Assignee: Bayer Aktiengesellschaft, Leverkusen, Fed. Rep. of Germany

[21] Appl. No.: 488,493

[22] Filed: Apr. 25, 1983

[30] Foreign Application Priority Data

May 8, 1982 [DE] Fed. Rep. of Germany ....... 3217387

[51] Int. Cl.³ ..................... C08G 18/64; C07D 235/30
[52] U.S. Cl. ....................................... 528/73; 548/307
[58] Field of Search ........................... 548/307; 528/73

[56] References Cited

U.S. PATENT DOCUMENTS 3,655,689 4/1972 Singer ................................ 548/307
3,822,282 7/1974 Singer ................................ 548/307

FOREIGN PATENT DOCUMENTS 1936157 9/1970 Fed. Rep. of Germany .

OTHER PUBLICATIONS

Houben–Weyl, Methoden der organischen Chemie, vol. XIV/2, 4th Edition, Georg Thieme Verlag, Stuttgart 1963, pp. 61–70.

*Primary Examiner*—H. S. Cockeram
*Attorney, Agent, or Firm*—Gene Harsh; Joseph C. Gil; Thomas W. Roy

[57] ABSTRACT

The present invention relates to a process for the production of compounds containing reversibly blocked and, optionally, free alcoholic hydroxyl groups, characterized in that organic compounds containing at least one alcoholic hydroxyl group, but otherwise being inert under the reaction conditions are reacted at 0° to 140° C. with N,N'-disubstituted 5-acylimino-imidazolidine diones. The present invention also relates to the use of these compounds for the production of polyurethanes.

6 Claims, No Drawings

PROCESS FOR THE PRODUCTION OF BLOCKED COMPOUNDS OPTIONALLY CONTAINING FREE HYDROXYL GROUPS AND THEIR USE FOR THE PRODUCTION OF POLYURETHANES

BACKGROUND OF THE INVENTION

1. Field of the Invention

This invention relates to a new process for the production of compounds containing blocked alcoholic hydroxyl groups and, optionally, free hydroxyl groups and to the use of compounds containing in all at least three such groups for the production of polyurethanes.

2. Description of the Prior Art

It is generally known that reactive systems which can be stored at room temperature and converted into high molecular weight polyurethanes under the effect of heat can be produced by mixing organic polyhydroxyl compounds containing preferably alcoholically bound hydroxyl groups with blocked polyisocyanates (cf. for example Houben-Weyl, Methoden der organischen Chemie, Vol. XIV/2, 4th Edition, Georg Thieme Verlag, Stuttgart 1963, pages 61–70). The disadvantage of this process, however, lies in the fact that volatile and, in many cases, even inflammable and physiologically harmful substances, i.e. the blocking agents used for blocking the isocyanate groups, are released during the thermal hardening of systems of the type in question. In addition, the use of systems such as these in coating compositions is attended by the disadvantage that the coating cannot be chemically dried, for example by the reaction of free isocyanate groups with atmospheric moisture, because the systems are largely inert even to atmospheric moisture at temperatures below the hardening temperature.

Accordingly, the object of the present invention is to provide new systems which are not attended by the disadvantages of conventional systems based on blocked polyisocyanates and free polyhydroxyl compounds, i.e. can be thermally converted into high molecular weight polyurethanes without the elimination of readily volatile blocking agents despite virtually indefinite storage at room temperature, and which by virtue of the presence of free isocyanate groups under "chemical drying" under the influence of atmospheric moisture before the actual thermal crosslinking process.

It has now surprisingly been found that this object can be achieved by combining the polyisocyanates containing free isocyanate groups of the type normally encountered in polyurethane chemistry with certain compounds containing blocked alcoholic hydroxyl groups obtained by the process described in detail hereinafter.

The compounds containing blocked alcoholic hydroxyl groups and, optionally, also free alcoholic hydroxyl groups obtained by the process according to the invention described in detail hereinafter are not only suitable for the above-mentioned application, they are also fungicidally active substances—this applies in particular to the products based on monohydric alcohols obtained by the process according to the invention—or high molecular weight, often rubber-like polymers which may be split up into their monomeric constituents by simple heating—this applies in particular to products based on polyhydric alcohols and at least difunctional N,N'-disubstituted 5-acyliminoimidazolidine diones obtained by the process according to the invention.

SUMMARY OF THE INVENTION

The present invention relates to a process for the production of compounds containing reversibly blocked and, optionally, free alcoholic hydroxyl groups, characterized in that organic compounds containing at least one alcoholic hydroxyl group, but otherwise being inert under the reaction conditions are reacted at about 0° to 140° C. with N,N'-disubstituted 5-acylimino-imidazolidine diones corresponding to the following general formula

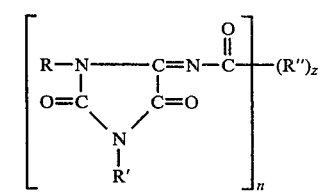

in which

R and R' may be the same or different and represent an optionally halogen-, $C_1$–$C_4$-alkyl-, methoxy-, nitro-, $C_1$–$C_4$-carbalkoxy- or nitrile-group-substituted aliphatic $C_1$–$C_{20}$ hydrocarbon radical, cycloaliphatic $C_3$–$C_{15}$ hydrocarbon radical, aromatic $C_6$–$C_{15}$ hydrocarbon radical or araliphatic $C_7$–$C_{15}$ hydrocarbon radical, R" represents an n-functional $C_2$–$C_{20}$, preferably $C_2$–$C_6$, hydrocarbon radical, cycloaliphatic $C_3$–$C_{15}$, preferably $C_6$, hydrocarbon radical, aromatic $C_6$–$C_{15}$, preferably $C_6$–$C_{10}$, hydrocarbon radical, araliphatic $C_7$–$C_{15}$, preferably $C_7$–$C_8$, hydrocarbon radical optionally containing inert substituents, a $C_1$–$C_4$ alkoxy radical optionally containing inert substituents, a phenoxy radical or a radical of the type obtained by removing the chlorocarbonyl groups from an n-functional organic carbamic acid chloride containing in all 2 to 10 carbon atoms, n=an integer of from 1 to 3 and z=0 or 1.

The present invention also relates to the use of the compounds containing in all at least two blocked and free hydroxyl groups obtained by this process for the production of polyurethanes.

DETAILED DESCRIPTION OF THE INVENTION

Any organic compounds containing at least one alcoholic hydroxyl group, but being otherwise inert under the conditions of the reaction according to the invention may be used in the process according to the invention. Preferred compounds of this type used in accordance with the invention are 2- to 6-hydric, more particularly 2- to 3-hydric, aliphatic alcohols optionally containing ether or ester bridges and having an (average) molecular weight of from about 62 to 5000 and preferably from about 62 to 3000, as calculated from the hydroxyl content and the functionality or, in the case of branched polyester polyols, as determined by osmometry. This means that the compounds containing alcoholic hydroxyl groups preferably used in accordance with the invention are the polyhydroxyl compounds known from polyurethane chemistry. However, in addition to these preferred polyhydroxyl compounds, it is also possible in the process according to the invention to use for example monohydric alcohols having a molecular weight in the range from about 32 to 300 and optionally containing inert substituents, higher than 6-hydric aliphatic alcohols or monohydric or polyhydric cycloaliphatic or araliphatic alcohols optionally containing inert substituents. The compounds containing hydroxyl groups used in the process according to the invention preferably contain solely primary and/or secondary hydroxyl groups.

The following are typical examples of compounds containing alcoholic hydroxyl groups suitable for use in accordance with the invention:

1. Primary or secondary monoalcohols, such as methanol, ethanol, propanol, butanol, isopropanol, isobutanol, 1-hexanol, 2-ethyl hexanol, 3-dimethylamino-1-propanol, 3-dimethylamino-2-propanol, glycol monomethyl ether, glycol monoethyl ether, 2-chloroethanol, 1,3-dichloro-2-propanol, 2,3-dibromo-1-propanol, 1-pentanol, 3-methyl-1-butanol, 2,2-dimethyl propanol, 4-methyl-2-pentanol, 1-octanol, 1-nonanol, 1-decanol, 1-dodecanol, 2-propen-1-ol, 9-octadecen-1-ol, 2-propyn-1-ol, 3-butyn-2-ol, cyclohexanol, 2-methyl cyclohexanol, 3-methyl cyclohexanol, cyclohexane methanol, 3,3,5-trimethyl cyclohexanol, decahydro-2-naphthol, borneol, isoborneol, benzyl alcohol and other monoalcohols of the type known from the literature (cf. for example Houben-Weyl, Vol. VI/1a).

2. Primary or secondary dihydroxy compounds containing alcoholic hydroxyl groups and having a molecular weight in the range from about 62 to 300, such as ethylene glycol, 2,2'-dihydroxy diethyl ether, 1,2-bis-(2-hydroxyethoxy)-ethane, tetraethylene glycol, bis-(2-hydroxyethyl)-sulfide, 1,2-propane diol, dipropylene glycol, tripropylene glycol, 3-chloro-1,2-propane diol, 1,3-propane diol, 1,2-butane diol, 1,3-butane diol, 1,4-butane diol, 2,3-butane diol, 1,5-pentane diol, 2,2-dimethyl-1,3-propane diol, 1,6-hexane diol, 2,5-hexane diol, 2,2-diethyl-1,3-propane diol, 1,12-octane diol, 2-butene-1,4-diol, 2-butyne-1,4-diol, 1,2-cyclohexane diol or 1,4-cyclohexane diol.

3. Primary and/or secondary trihydric or polyhydric alcohols having a molecular weight in the range from about 92 to 350, such as glycerol, 2-hydroxy methyl-2-methyl-1,3-propane diol, 1,2,6-hexane triol, 2-ethyl-2-hydroxymethyl-1,3-propane diol, 2,2-bis-hydroxymethyl-1,3-propane diol, sorbitol, mannitol, cane sugar, glucose and fructose.

4. Polyester or polyether polyols having a molecular weight in the range from about 300 to 5000 and preferably in the range from about 1000 to 3000 and generally containing from 2 to 6 and preferably from 2 to 3 alcoholic hydroxyl groups, of the type known per se from polyurethane chemistry (cf. for example U.S. Pat. No. 4,218,543, herein incorporated by reference, column 7, line 29 to column 9, line 25).

Reactants for these compounds containing alcoholic hydroxyl groups are N,N'-disubstituted 5-acylimino-imidazolidine diones corresponding to the above general formula. Preferred compounds of this type are those corresponding to the above general formula in which R and R' may be the same or different and each represent alkyl groups containing from 1 to 4 carbon atoms, R" represents an n-functional, unsubstituted, saturated aliphatic hydrocarbon radical containing from 1 to 6 carbon atoms or an n-functional, unsubstituted aromatic hydrocarbon radical containing 6 carbon atoms, n=1 or 2 and z=1.

The following are mentioned as examples of N,N'-disubstituted 5-acylimino-imidazolidine diones suitable for use in the process according to the invention: N,N'-dimethyl-5-acetylimino-imidazolidine dione, N,N'-dibutyl-5-acetylimino-imidazolidine dione, N,N'-distearyl-5-acetylimino-imidazolidine dione, N,N'-dimethyl-5-benzoylimino-imidazolidine dione, N,N'-dibutyl-5-benzoylimino-imidazolidine dione, the 2:1-reaction product of N,N'-dibutyl-5-trimethyl silylimino-imidazolidine dione with succinic acid dichloride, the 2:1-reaction product of N,N'-dibutyl-5-trimethyl silyl-imino-imidazolidine dione with adipic acid dichloride, the 2:1-reaction product of N,N'-dimethyl-5-trimethyl silyl-imino-imidazolidine dione with terephthalic acid dichloride or the 3:1-reaction product of N,N'-dimethyl-5-trimethyl silyl-imino-imidazolidine dione with trimesic acid trichloride.

The N,N'-disubstituted 5-acylimino-imidazolidine diones are known in principle, for example from DE-OS No. 1,936,157. They may be produced either by reacting 5-imino-imidazolidine diones with ketenes or by reacting 5-trimethyl-silyl-imino-imidazolidine diones with acid halides (cf. German Patent Application P 32 11 911.9).

In the reaction according to the invention, the alcoholic hydroxyl group is added onto the 5-acylimino group, as explained by way of example in the following with reference to the reaction between N,N'-dimethyl-5-acetylimino-imidazolidine dione and ethanol:

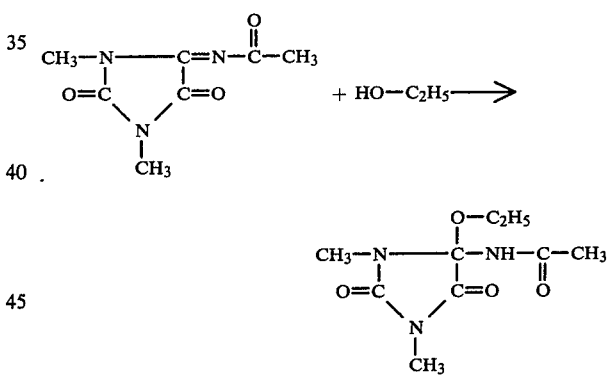

This addition reaction is reversible so that, when heated to temperatures above 140° C., the addition compounds release the added alcohol.

The process according to the invention may be carried out in the presence or absence of solvents. Suitable solvents are, for example halogenated hydrocarbons, such as methylene chloride, chloroform, trichloroethane, chlorobenzene, 1,2-dichlorobenzene, toluene, xylene, hexane, petroleum ether, mineral spirits, petrol and petrol mixtures of the type used in the lacquer industry, ethyl glycol acetate, glycol monomethyl ether acetate and/or mixtures of these solvents. Where readily distillable monohydric alcohols are employed in the process according to the invention, they may even be used in a large excess, in which case the excess quantities perform the function of a solvent.

The reaction according to the invention may be carried out at temperatures in the range from about 0° to 140° C., preferably at temperatures in the range from about 20° to 130° C., and more preferably, at temperatures in the range from about 80° to 110° C.

In the practical application of the process according to the invention, the reactants are generally used in quantities corresponding to an equivalent ratio of hydroxyl groups to imidazolidine dione structural units of from about 0.9:1 to 2:1, preferably from about 0.9:1 to 1.5:1 and more preferably about 1:1. It is only in cases where monohydric alcohols are employed that these alcohols may be used in a large excess, as already mentioned.

The choice of the type of starting materials used in the process according to the invention and the quantitative ratios in which they are used is determined primarily by the purpose for which the products obtained by the process according to the invention are intended.

Products obtained by the process according to the invention which are to be used in accordance with the invention, i.e. which are to be combined with organic polyisocyanates to form heat-crosslinkable systems, are produced using at least dihydric alcohols or mixtures of at least dihydric alcohols of the type mentioned by way of example above with the monofunctional blocking agents (n=1) essential to the invention. In this connection, it is not necessary to block all of the free hydroxyl groups, so that it is even possible to work within the above-mentioned limits using an excess of hydroxyl compounds. Partly blocked polyhydroxyl compounds obtained in this way naturally react only partly with the polyisocyanate at temperatures below 140° C., more particularly at room temperature, so that systems still capable of being processed are obtained even after this partial reaction. An incomplete preliminary reaction such as this (addition of some of the isocyanate groups onto the free hydroxyl groups) may be desirable in special cases, for example when it is intended to produce highly viscous systems, for example sealing compounds, which are only converted into the crosslinked state at elevated temperatures.

In cases where polyhydric alcohols are used in combination with at least difunctional blocking agents (n=2 or 3) essential to the invention, new, high molecular weight, often rubber-like polymers are formed for an equivalent ratio of from about 0.9:1 to 1.1:1, more particularly of the order of about 1:1, decomposing into their monomeric constituents on heating to temperatures above 140° C.

The reaction of monohydric alcohols of the type mentioned by way of example in the foregoing with the blocking agents essential to the invention gives new compounds which show surprising fungicidal activity. These process products according to the invention based on monohydric alcohols may thus be used as fungicidally active substances.

The products obtained by the process according to the invention may generally be used, for example in accordance with the invention, without any need for further purification, optionally after the solvent used has been removed by distillation.

Where the products obtained by the process according to the invention, which contain in all at least two blocked and free hydroxyl groups, are used in accordance with the invention, they are mixed for example with the polyisocyanates known per se from polyurethane chemistry in an equivalent ratio of isocyanate groups to free and blocked hydroxyl groups of from about 2:1 to 0.5:1 and preferably from about 1.1:1 to 0.9:1. The auxiliaries and additives known per se from polyurethane chemistry, such as for example solvents, pigments, fillers, levelling aids and the like, may be additionally added to the resulting mixtures.

Organic isocyanates particularly suitable for the use according to the invention are, in particular, 2,4- and/or 2,6-diisocyanatotoluene, 4,4'-diisocyanatodiphenyl methane and its technical mixtures with 2,4'-diisocyanatodiphenyl methane and/or higher homologs, hexamethylene diisocyanate, a biuret polyisocyanate based on hexamethylene diisocyanate, isophorone diisocyanate or 4,4'-diiosocyanatocyclohexyl methane. NCO-prepolymers which may be obtained in known manner by reacting an excess of polyisocyanates of the type exemplified hereinbefore with polyhydroxyl compounds of the type exemplified hereinbefore under 2.–4. may also be used.

The use according to the invention of the products obtained by the process according to the invention for the production of polyurethane is particularly suitable for the production of heat-cross-linkable stoving lacquers. Apart from the generally untroublesome preliminary reaction between some of the isocyanate groups and the free hydroxyl groups present, if any, stoving lacquers of this type may be stored virtually indefinitely at temperatures below 140° C., more particularly at room temperature, and may be processed at any time after their production. Coatings applied to heat-resistant substrates with systems such as these by any of the methods normally used in lacquer technology harden after heating for about 15 to 60 minutes to temperatures above 140° C., more particularly to temperatures in the range from about 145° to 180° C., to form high-quality lacquer coatings. The blocking agents essential to the invention which are released as a result are substantially involatile compounds which remain in the lacquer film, even under the above-mentioned stoving conditions, without in any way adversely affecting its lacquer properties.

The invention is further illustrated by the following Examples in which all the percentages quoted represent percentages by weight, unless otherwise indicated.

EXAMPLES

Example 1

100 g (0.294 hydroxyl equivalents) of a standard commercial polyester (molecular weight 1580, as determined by osmometry) of phthalic acid anhydride, maleic acid anhydride (molar ratio=2.1) and trimethylol propane in the form of a 65% solution in ethyl glycol acetate (OH-number 165) are stirred for 5 hours at 100° C. with 78.5 g of N,N'-dibutyl-5-acetylimino-imidazolidine dione (0.294 mole). A clear viscous solution is obtained after cooling to room temperature. OH-number: 11.

Example 2

20 g (corresponding to 0.033 OH-equivalents, based on blocked and free hydroxyl groups) of the reaction product of Example 1 are mixed with 6.2 g of a low-viscosity biuretized hexamethylene diisocyanate having an NCO-content of 23.4% (corresponding to 0.035 NCO-equivalents), the resulting mixture diluted with 20 g of a mixture of ethyl glycol acetate and xylene (1:1) and coated onto a plate. After hardening for 30 minutes at 150° C., a clear, oven-dry elastic film is obtained. The film thus obtained is not dissolved by acetone or xylene.

The mixture can still be effectively processed after storage for 2 months at 25° C.

COMPARISON EXAMPLE 20 g of the polyester used in Example 1 (corresponding to 0.059 OH-equivalents) are mixed with 10.6 g of the low-viscosity biuretized hexamethylene diisocyanate (corresponding to 0.062 NCO-equivalents) and the resulting mixture diluted with 20 g of ethyl glycol acetate/xylene 1:1. The mixture hardens to form a rubber-like material after 1 day at 25° C.

Example 3

98.7 g (0.3 mole) of N,N'-dibutyl-5-benzoyliminoimidazolidine dione are refluxed for 2 hours in 100 ml of methanol. After removal of the excess methanol by distillation, the oily residue is mixed with cleaning spirit, and the colorless crystals are filtered off under suction and dried.

Yield: 93.5 g (86.6% of the theoretical);
M.p.: 84°–86° C.
$C_{19}H_{26}N_3O_4$ observed C 63.3%, H 7.2%, N 11.7%; calculated C 63.3%, H 7.3%, N 11.6%.

Example 4

90 g (0.25 mole) of the product of Example 3 are heated to 145° C. in a gentle stream of nitrogen. The distillate is collected in a cold trap. Distillate: 7.6 g of methanol (95.0% of the theoretical). The residue is identified as N,N'-dibutyl-5-benzoyliminoimidazolidine dione.

Yield: 82.3 g (theoretical: 82.25 g).

Example 5

66.8 g (0.25 mole) of N,N'-dibutyl-5-acetyliminoimidazolidine dione are stirred for 30 minutes at 80° C. in 150 ml of methanol. After removal of the excess methanol by distillation, the product is precipitated from cleaning spirit.

Yield: 72.3 g (96.7% of the theoretical);
M.p.: 111° C.

Example 6

29.9 g (0.1 mole) of the product of Example 5 and 11.9 g (0.1 mole) of phenyl isocyanate are heated to 130° C. in 50 ml of ortho-dichlorobenzene. There is no evidence of any reduction in the isocyanate content of the mixture. The mixture is heated to 140° C., the isocyanate content being completely reduced to form N-phenyl methyl urethane and N,N'-dibutyl-5-acetyliminoimidazolidine dione.

Example 7

500 g (0,25 mole) of a polyether polyol obtained by propoxylation of 1,2-dihydroxy-propane and subsequent ethoxylation of the propoxylation product (molar ratio propylene oxid/ethylene oxide=95:5) having an OH number of 56 and a viscosity at 25° C. of 300 cP are admixed at 100° C. with 133,5 g (0,5 mole) of 5-acetylmino-N-N'-dibutyl-imidazolidin dione. After a reaction time of 10 h no free hydroxyl groups remain behind.

Example 8

200 g of the reaction product of example 7 are admixed with 20 g of ethyl glycol acetate and 3,03 g of a biuret polyisocyanate consisting essentially of tris-(isocyanatohexyl)-biuret and having an NCO-content of 22,98%. A glass plate is coated with this mixture and the coating thus obtained is stoved for 30 minutes at 160° C. A soft very elastic coating is obtained.

Example 9

140 g of a polyester polyol having OH number of 290 obtained by reacting adipic acid, phthalic acid anhydride and maleic acid anhydride with 1,2-dihydroxypropane and trimethylol propane are dissolved in 60 g of ethyl glycol acetate. Thereafter 166,6 g of 5-acetylimino-N,N'-dibutyl-imidazolidin-dione are added to the solution under stirring at 100° C. After a reaction time of 8 h at 100° C. no free hydroxyl groups remained behind.

Example 10

20 g of the product of example 9, 20 g of ethyl glycol acetate and 6,53 g of the biuret polyisocyanate of example 8 are admixed. Thereafter a glass plate is coated with this mixture. The coating is stoved for 30 minutes at 160° C. A clear, colourless and solvent-resistant coating is obtained.

Example 11

80,1 g (0,3 mole) of 5-acetylimino-N,N'-dibutyl-imidazolidin-dione, 100 ml of toluene and 9,2 g (0,1 mole) of glycerol are stirred for 16 h at 120° C. Subsequently the toluene is distilled off under a pressure of 20 mbar. A yellowish, highly viscous residue remains behind which does no longer contain free hydroxyl groups.

Example 12

45 g (0,5 mole) of 1,4-dihydroxybutane, 267 g (1 mole) of 5-acetylimino-N,N'-dibutylimidazolidin-dione and 200 ml of toluene are stirred for 8 h at 120° C. Subsequently the toluene is stilled off under vacuum. The residue is dried at 70° C. under vacuum. Finally a solid, white residue is obtained which does no longer contain free hydroxyl groups and which has a melting point of 137° C.

Example 13

7,06 g of the product of example 12 are dissolved in 35 g of dichloromethane. Simultaneously an excess amount of the biuret polyisocyanate of example 8 is reacted with a polyester polyol based on phthalic acid anhydride, maleic acid unhydride and trimethylol propane (hydroxyl number: 260) so that an NCO-prepolymer is obtained which exhibits an NCO-content of 9,5%. The NCO-prepolymer is dissolved in a mixture of ethyl glycol acetate/xylene (4:1) to form a 60% solution. 10 g of this solution is admixed with the solution of the product of example 12 (equivalent ratio of NCO-groups/blocked hydroxyl groups=1:1). The mixture is brushed on a glass plate and the coating thus obtained is stoved for 30 minutes at 150° C. A clear, elastic and acetone-resistant coating is obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of compounds containing reversibly blocked and, optionally, free alcoholic hydroxyl groups, characterized in that organic compounds containing at least one alcoholic hydroxyl group, but being otherwise inert under the reaction conditions are reacted at about 0° to 140° C. with N,N'-disubstituted 5-acylimino-imidazolidine diones corresponding to the following general formula

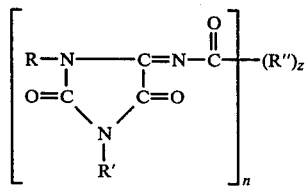

in which
R and R' may be the same or different and represent an optionally halogen-, $C_1$-$C_4$-alkyl, methoxy-, nitro-, $C_1$-$C_4$-alkoxy- or nitrile-group-substituted aliphatic $C_1$-$C_{20}$ hydrocarbon radical, cycloaliphatic $C_3$-$C_{15}$ hydrocarbon radical, aromatic $C_6$-$C_{15}$ hydrocarbon radical or araliphatic $C_7$-$C_{15}$ hydrocarbon radical, R" represents an n-functional aliphatic $C_2$-$C_{20}$ hydrocarbon radical, cycloaliphatic $C_3$-$C_{15}$ hydrocarbon radical, aromatic $C_6$-$C_{15}$ hydrocarbon radical, araliphatic $C_7$-$C_{15}$ hydrocarbon radical optionally containing inert substituents, a $C_1$-$C_4$ alkoxy radical optionally containing inert substituents, a phenoxy radical or a radical of the type obtained by removal of the chlorocarbonyl groups from an n-functional organic carbamic acid chloride containing a total of 2 to 10 carbon atoms, n=an integer of from 1 to 3 and
z=0 or 1.

2. The process as claimed in claim 1, characterized in that the N,N'-disubstituted 5-acylimino-imidazidine diones used are those corresponding to the formula in claim 1 in which
R and R' may be the same or different and each represent an aliphatic $C_1$-$C_4$ hydrocarbon radical,
R" represents an n-functional, unsubstituted, saturated aliphatic $C_1$-$C_6$ hydrocarbon radical or an n-functional, unsubstituted, aromatic $C_6$ hydrocarbon radical,
n=1 or 2 and
z=1.

3. The process as claimed in claim 1, characterized in that aliphatic alcohols containing 2 to 6 hydroxyl groups, having a molecular weight of from about 62 to 5000 and optionally containing ether or ester bridges or mixtures of these alcohols are used as the compounds containing alcoholic hydroxyl groups.

4. The process as claimed in claim 1, characterized in that the reactants are used in quantities corresponding to an equivalent ratio of alcoholic hydroxyl groups to imidazolidine dione structural units of from about 0.9:1 to 1.5:1.

5. The process of claim 1 wherein R" represents an n-functional aliphatic $C_2$-$C_6$ hydrocarbon radical, cycloaliphatic $C_6$ hydrocarbon radical, aromatic $C_6$-$C_{10}$ hydrocarbon radical or araliphatic $C_7$-$C_8$ hydrocarbon radical optionally containing inert substituents.

6. A process for the production of a polyurethane which comprises
(a) preparing a compound containing at least two partially blocked hydroxyl groups according to the process of claim 3,
(b) mixing the compounds prepared in (a) with an organic polyisocyanate and
(c) heating the mixture formed in (b) to a temperature in excess of 140° C.

* * * * *